United States Patent
Schaeffer

(10) Patent No.: US 9,937,330 B2
(45) Date of Patent: Apr. 10, 2018

(54) SYSTEM, METHOD, AND KIT FOR PROVIDING THE DIAMETER OF A BALLOON DURING TREATMENT

(71) Applicant: Cook Medical Technologies LLC, Bloomington, IN (US)

(72) Inventor: Darin Schaeffer, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 227 days.

(21) Appl. No.: 14/270,655

(22) Filed: May 6, 2014

(65) Prior Publication Data

US 2014/0336617 A1    Nov. 13, 2014

Related U.S. Application Data

(60) Provisional application No. 61/820,374, filed on May 7, 2013.

(51) Int. Cl.
*A61M 25/10* (2013.01)
*A61B 5/107* (2006.01)
(Continued)

(52) U.S. Cl.
CPC ..... *A61M 25/10188* (2013.11); *A61B 5/1076* (2013.01); *A61B 5/6853* (2013.01);
(Continued)

(58) Field of Classification Search
CPC ........ A61M 25/1018; A61M 25/10182; A61M 25/10187; A61M 25/10188;
(Continued)

(56) References Cited

U.S. PATENT DOCUMENTS 5,019,041 A    5/1991   Robinson et al.
5,163,904 A   11/1992   Lampropoulos et al.
(Continued)

FOREIGN PATENT DOCUMENTS

EP    2080474       7/2009
WO    03090836    11/2003
(Continued)

OTHER PUBLICATIONS

Oxford Dictionary definition for "nominal value". available online as of Jul. 27, 2016 at http://www.oxforddictionaries.com/us/definition/american_english/nominal-value.*
(Continued)

*Primary Examiner* — Emily Schmidt
*Assistant Examiner* — Amber Stiles
(74) *Attorney, Agent, or Firm* — Buchanan Van Tuinen LLC

(57) ABSTRACT

Medical systems are described herein. More particularly, the disclosure relates to medical systems, methods, and kits useful in providing the diameter of a balloon during the performance of a procedure. An exemplary medical system comprises a balloon catheter, an inflation device, and a measuring device having one or more indicia. Each indicium of the one or more indicia has a form that corresponds to the nominal value of a balloon diameter.

20 Claims, 6 Drawing Sheets

(51) Int. Cl.
*A61B 5/00* (2006.01)
*A61F 2/24* (2006.01)

(52) U.S. Cl.
CPC .... *A61F 2/2496* (2013.01); *A61F 2250/0039* (2013.01); *A61M 25/10182* (2013.11); *A61M 2205/3331* (2013.01); *A61M 2205/583* (2013.01); *A61M 2205/6081* (2013.01)

(58) Field of Classification Search
CPC ...... A61M 2205/50; A61M 2205/6081; A61M 2205/583; A61M 2205/3331
See application file for complete search history.

(56) References Cited

U.S. PATENT DOCUMENTS

| | | | |
|---|---|---|---|
| 5,171,299 A * | 12/1992 | Heitzmann | A61M 25/104 604/100.03 |
| 5,259,838 A * | 11/1993 | Taylor | A61M 25/10182 604/100.03 |
| 5,318,533 A | 6/1994 | Adams et al. | |
| 5,449,344 A | 9/1995 | Taylor et al. | |
| 5,470,317 A | 11/1995 | Cananzey et al. | |
| 6,110,200 A * | 8/2000 | Hinnenkamp | A61F 2/2496 33/512 |
| 6,190,354 B1 * | 2/2001 | Sell | A61M 25/1018 604/532 |
| 7,314,461 B2 | 1/2008 | Carter et al. | |
| 7,856,730 B2 * | 12/2010 | Sakai | A61B 5/1076 33/542 |
| 9,125,801 B2 | 9/2015 | Bhagchandani | |
| 2004/0019323 A1 * | 1/2004 | Carter | A61M 25/1018 604/97.03 |
| 2004/0230157 A1 | 11/2004 | Perry et al. | |
| 2006/0063973 A1 | 3/2006 | Makower et al. | |
| 2006/0064039 A1 | 3/2006 | Griego et al. | |
| 2009/0076439 A1 | 3/2009 | Dollar et al. | |
| 2010/0179488 A1 * | 7/2010 | Spiegel | A61M 16/044 604/240 |
| 2012/0017897 A1 | 1/2012 | Ranganathan et al. | |
| 2014/0074021 A1 | 3/2014 | Bhagehandani | |
| 2014/0081205 A1 * | 3/2014 | Kanner | A61M 25/1018 604/97.02 |

FOREIGN PATENT DOCUMENTS

| | | |
|---|---|---|
| WO | 2004006767 | 1/2004 |
| WO | 2009036424 | 3/2009 |
| WO | 2009137225 | 11/2009 |
| WO | 2011142758 | 11/2011 |

OTHER PUBLICATIONS

European Patent Office, Extended Search Report and Written Opinion for Application No. 14167411.9. dated Jul. 22, 2014.

* cited by examiner

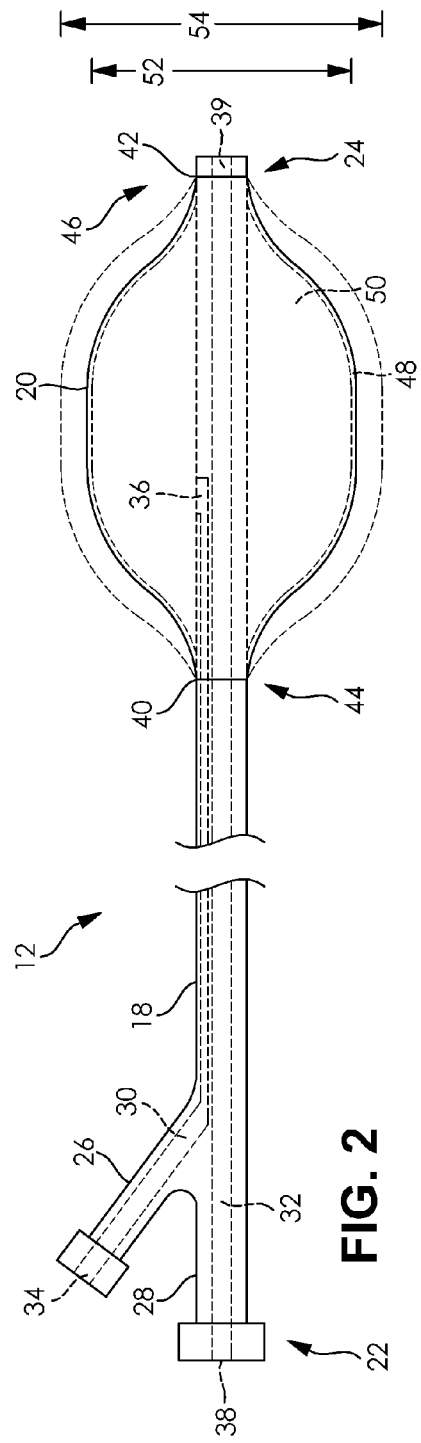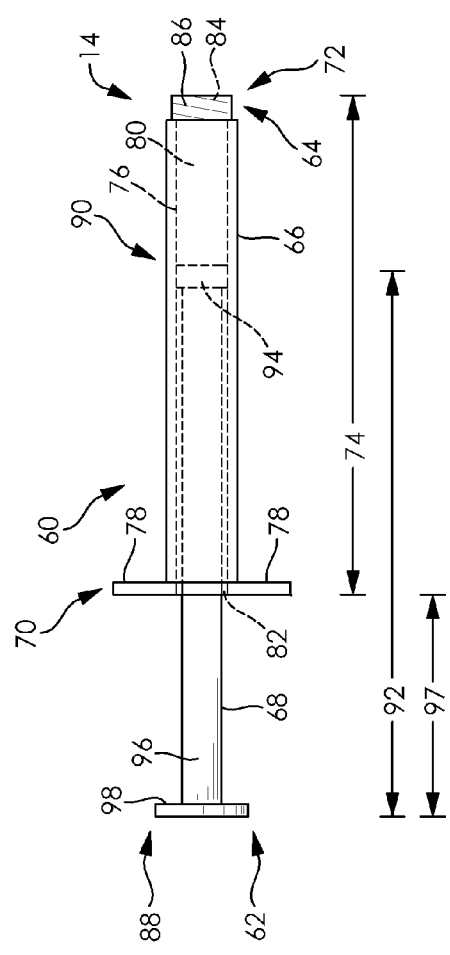

SYSTEM, METHOD, AND KIT FOR PROVIDING THE DIAMETER OF A BALLOON DURING TREATMENT

RELATED APPLICATION

This application claims the benefit of U.S. Provisional Application No. 61/820,374, filed May 7, 2013. The disclosure of this related application is hereby incorporated into this disclosure in its entirety.

FIELD

The disclosure relates generally to medical devices. More particularly, the disclosure relates to systems for providing the diameter of a balloon during treatment of a bodily passage, such as a body vessel, airway, sinus cavity, sinus passage, or the gastrointestinal (GI) tract. The disclosure also relates to methods and kits useful in providing the diameter of a balloon during treatment of a bodily passage.

BACKGROUND

It is sometimes necessary or otherwise desirable to dilate a bodily passage, such as an airway, using a balloon catheter. For example, when an airway becomes narrowed, balloon dilation—the dilation of the airway using a balloon catheter—provides an alternative to radical surgical approaches for opening the airway. Conventional dilation procedures advance a balloon catheter over a previously-placed wire guide and move the balloon to an inflated configuration to effectuate dilation. However, these procedures are complicated by the need to determine the diameter of the balloon during the procedure, which can cause damage to the bodily passage if overinflated or fail to provide the necessary dilation if underinflated.

One method of determining the diameter of the balloon during treatment is to inflate the balloon with an inflation device containing a pressure gauge. However, this approach has significant drawbacks because it requires the use of a pressure gauge that provides a numerical value representing the pressure of a fluid disposed within the balloon. A user must observe the numerical value representing the pressure and subsequently reference the device labeling to determine the diameter of the balloon. This is accomplished, for example, by referencing a chart or table that correlates the numerical value representing the pressure with a diameter of the balloon. This increases the potential for human error during the conversion process between pressure and diameter and increases the time and complexity of the procedure.

Therefore, a need exists for improved systems, methods, and kits for providing the diameter of a balloon during treatment.

SUMMARY

Various exemplary medical systems are described.

An exemplary medical system comprises a balloon, inflation device, and a measuring device. The balloon has a balloon wall that defines a balloon chamber and is moveable between a first deflated configuration and a second inflated configuration as a fluid moves into and out of the balloon chamber. The balloon has an inflated balloon diameter in the second inflated configuration. The inflation device is operatively connected to the balloon and is adapted to move the balloon between the first deflated configuration and the second inflated configuration. The measuring device is operatively connected to the balloon and is in fluid communication with the balloon chamber. The measuring device is adapted to measure the pressure of the fluid disposed within the balloon chamber and has a measuring device body, a plurality of indicia disposed on the measuring device body, and an indicator. The indicator is moveable on the measuring device relative to the plurality of indicia and between an indicator first position when the balloon is in the first deflated configuration and the fluid within the balloon chamber has a first pressure and an indicator second position when the balloon is in the second inflated configuration and the fluid within the balloon chamber has a second pressure. The second pressure is greater than the first pressure. In the indicator second position, the indicator is positioned relative to an indicium of the plurality of indicia that corresponds to the inflated balloon diameter.

In addition, various methods of treatment and kits are described.

Additional understanding of the exemplary medical systems, methods, and kits can be obtained by review of the detailed description, below, and the appended drawings.

BRIEF DESCRIPTION OF THE FIGURES

FIG. 2 is a side view of the balloon catheter illustrated in FIG. 1.

FIG. 3 is a side view of the inflation device illustrated in FIG. 1.

DETAILED DESCRIPTION

Figure 1:
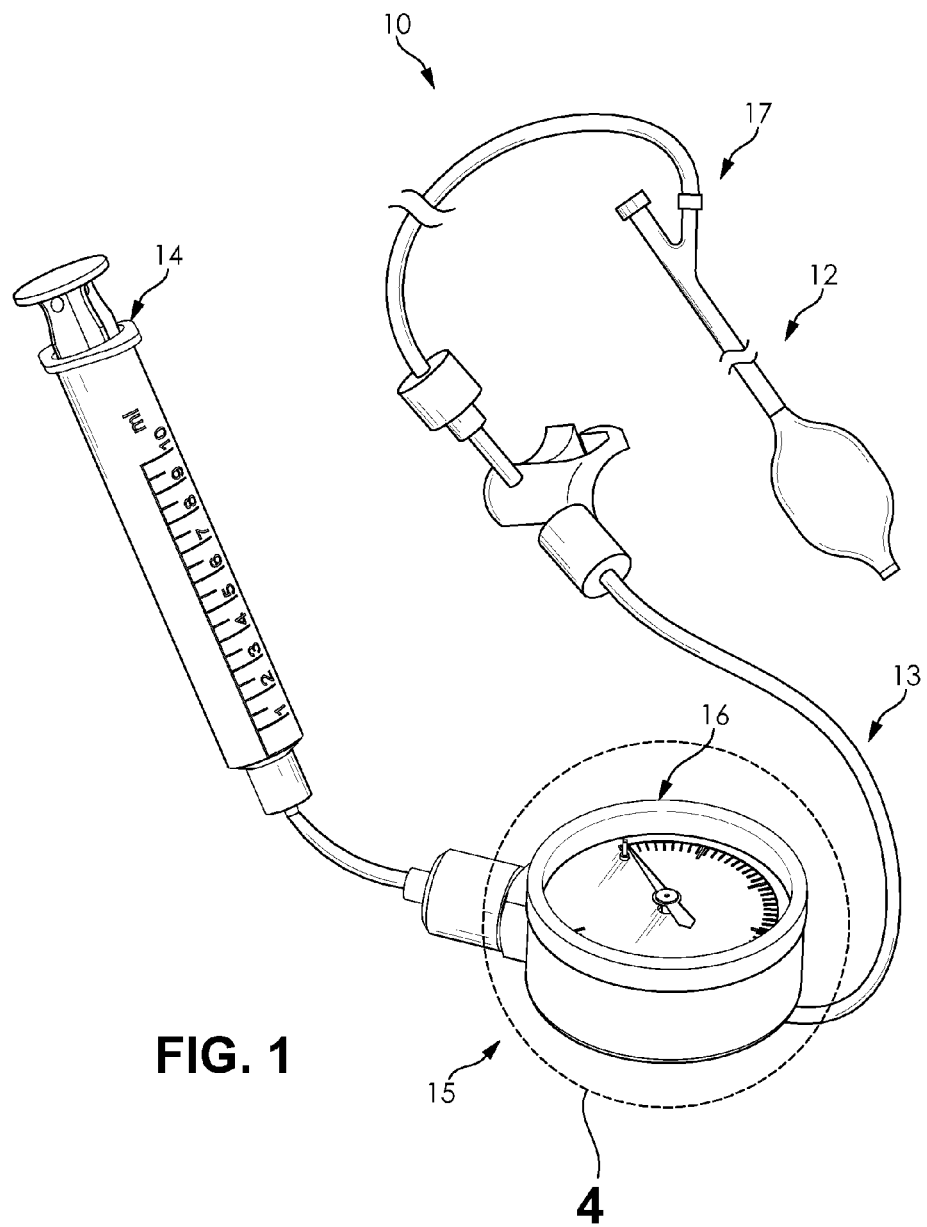
FIG. 1 is a perspective view of an exemplary medical system.

The following detailed description and the appended drawings describe and illustrate various exemplary medical systems, methods, and kits. The description and drawings are exemplary in nature and are provided to enable one skilled in the art to make and use one or more exemplary medical systems, practice one or more exemplary methods, and/or provide one or more kits. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "exemplary" refers to "an example of" and is not intended to convey a meaning of an ideal or preferred embodiment. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular elements or features being described. The use of "bodily passage" or "body passage" refers to any passage within the body of an animal, including, but not limited to, humans, and includes elongate passages and any portion of the gastrointestinal (GI) tract. The term "sinus passage" refers to the nasal passages, and includes, but is not limited to, eustachian tube(s), primary ostium, accessory ostium, and/or an opening defined by a ventilation tube. The term "airway" refers to any airway including, but not limited to, the nasopharynx, oropharynx, pharynx, trachea, bronchial tubes, esophagus, esophageal tract, and/or lungs. The term "sinus cavity" refers to the frontal, ethmoid, sphenoid, and/or maxillary sinus.

FIGS. 1, 2, 3, 4, and 4A illustrate an exemplary medical system 10 for providing the diameter of a balloon during treatment. The system 10 comprises a balloon catheter 12, an extension tube 13, an inflation device 14, and a measuring device 16.

Balloon catheter 12 comprises an elongate member 18 and a balloon 20.

Elongate member 18 can have any suitable outside diameter and length, and skilled artisans will be able to select a suitable outside diameter and length for an elongate member according to a particular embodiment based on various considerations, including the desired bodily passage within which the elongate member is intended to be used.

Elongate member 18 can be formed of any suitable material, and skilled artisans will be able to select a suitable material to form an elongate member according to a particular embodiment based on various considerations, including the desired flexibility of the elongate member. Example materials considered suitable to form an elongate member include, but are not limited to, biocompatible materials, materials that can be made biocompatible, metals such as stainless steel, titanium, polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular application.

In the illustrated embodiment, the elongate member 18 comprises an elongate member proximal end 22, an elongate member distal end 24, and defines an inflation port 26, a device port 28, an inflation lumen 30, and a device lumen 32.

Inflation port 26 and device port 28 are disposed on a proximal portion of elongate member 18 and can include any suitable connector and/or adapter capable of attaching, or assisting with attaching, one or more devices to elongate member 18. Skilled artisans will be able to select a suitable connector and/or adapter to include on an inflation port and/or device port of an elongate member according to a particular embodiment based on various considerations, including the material(s) that forms the elongate member. Example connectors and/or adapters considered suitable to include on an inflation port and/or device port of an elongate member include, but are not limited to, threaded connectors, Tuohy Borst adapters, luer lock connectors, and any other connector and/or adapter considered suitable for a particular application.

Inflation lumen 30 extends from a first inflation lumen opening 34 defined on the inflation port 26 to a second inflation lumen opening 36 defined between the elongate member proximal end 22 and the elongate member distal end 24. Device lumen 32 extends from a first device lumen opening 38 defined on the device port 28 to a second device lumen opening 39 defined on the elongate member distal end 24.

While elongate member 18 has been illustrated as having a bifurcated structural configuration defining an inflation port, a device port, an inflation lumen, and a device lumen, an elongate member can have any suitable structural configuration defining any suitable number of ports and/or lumens. Skilled artisans will be able to select a suitable structural configuration and number of ports and/or lumens to include on an elongate member according to a particular embodiment based on various considerations, including the procedure intended to be performed. Example number of ports and/or lumens considered suitable to include on an elongate member include, but are not limited to, one, at least one, two, a plurality, three, four, and any other number considered suitable for a particular application. For example, an elongate member can define a wire guide lumen adapted to receive a wire guide that extends from a first opening on elongate member proximal end to a second opening on elongate member distal end. Optionally, device lumen 32 can be used to advance a device (e.g., guide wire) through balloon catheter 12.

Balloon 20 can be formed of any suitable material, and skilled artisans will be able to select a suitable material to form a balloon according to a particular embodiment based on various considerations, including the material(s) that forms an elongate member. Example materials considered suitable to form a balloon include, but are not limited to, biocompatible materials, materials that can be made biocompatible, flexible materials, substantially flexible materials, polymers, Pebax (Pebax is a registered trademark of Ato Chimie Corporation of Allee des Vosges, Courbevoie, France), nylon, polyethylene, polyurethane, and any other material considered suitable for a particular application.

In the illustrated embodiment, balloon 20 is attached to elongate member 18 between the elongate member proximal end 22 and the elongate member distal end 24 at a balloon proximal junction 40 and a balloon distal junction 42. Balloon 20 comprises a balloon proximal end 44, a balloon distal end 46, and a balloon wall 48. Balloon wall 48 and the portion of the exterior surface of elongate member 18 disposed within balloon 20 define a balloon chamber 50 that is adapted to receive a fluid such that balloon 20 can be moved between a first deflated configuration and a second inflated configuration as fluid moves into and out of the balloon chamber, as described in more detail herein. FIG. 2 illustrates balloon 20 in the second inflated configuration.

Balloon 20 is attached to elongate member 18 such that the second inflation lumen opening 36 is in fluid communication with balloon chamber 50. With this structural arrangement, balloon 20 is adapted to move between the first deflated configuration and the second inflated configuration as fluid is moved into and out of balloon chamber 50 via the inflation lumen 30 and second inflation lumen opening 36.

Balloon proximal junction 40 and balloon distal junction 42 can comprise any suitable method of attachment between elongate member 18 and balloon 20, and skilled artisans will be able to select a suitable method of attachment between a balloon and an elongate member according to a particular embodiment based on various considerations, including the material(s) that forms the elongate member and balloon. Example methods of attachment considered suitable between an elongate member and a balloon include, but are not limited to, attachments formed by heat fusing, using adhesives, mechanical connections, and any other method considered suitable for a particular application.

A user inflates balloon 20 by introducing a fluid, such as saline, into the inflation lumen 30 until the fluid passes through second inflation lumen opening 36 and into balloon chamber 50. The resulting pressure placed on the inner surface of balloon 20 by the fluid causes the balloon 20 to inflate and adopt the second inflated configuration. To move the balloon 20 to the first deflated configuration, vacuum pressure can be applied to the inflation lumen 30 to remove the fluid located within the balloon chamber 50 via the second inflation lumen opening 36, resulting in the balloon 20 collapsing and adopting the first deflated configuration.

Balloon 20 has a lengthwise axis, an axial length extending along the lengthwise axis of elongate member 18, and defines an inflated balloon diameter 52 when balloon 20 is in the second inflated configuration. Balloon 20 also defines a deflated balloon diameter (e.g., zero, diameter of balloon when no fluid is disposed within, or is being introduced into, the balloon chamber, diameter of balloon when the balloon chamber is at atmospheric pressure) when the balloon 20 is in the deflated configuration. The deflated balloon diameter of the balloon 20 is less than the inflated balloon diameter 52 when the balloon 20 is in the second inflated configuration. Each of the deflated balloon diameter and the inflated balloon diameter 52 is measured along a plane that is disposed orthogonal, or substantially orthogonal, to the lengthwise axis of balloon 20. The inflated balloon diameter 52 is relative to the pressure of the fluid contained within the balloon chamber 50, as described in more detail herein. Thus, the inflated balloon diameter 52 can vary depending on the pressure of the fluid contained within the balloon chamber 50. Balloon 20 has an inflated balloon maximum diameter 54, illustrated in phantom lines in FIG. 2, which represents the maximum diameter of the balloon 20 (e.g., a diameter that should not be exceeded during performance of a procedure to prevent rupture of the balloon).

Each of the balloon inflated diameter 52 and the inflated balloon maximum diameter 54 is measurable using any suitable unit of length, and skilled artisans will be able to select a suitable unit of length to measure a balloon diameter according to a particular embodiment based on various considerations, including the material(s) that forms a balloon. Example units of length considered suitable to measure a balloon diameter include, but are not limited to, United States customary units, the Metric System, the International System of Units, the French Scale, Imperial units, and any other unit of length considered suitable for a particular application.

While the balloon catheter 12 has been illustrated as having a particular structural configuration, any suitable balloon catheter having any suitable structural configuration can be used with the medical systems, methods, and/or kits described herein. Skilled artisans will be able to select a suitable balloon catheter, and structural configuration for a balloon catheter, according to a particular embodiment based on various considerations, including the procedure intended to be performed.

Additional structure is attached to balloon catheter 12 to facilitate the inflation and deflation of the balloon 20, as described above. In the illustrated embodiment, an extension tube 13 and an inflation device 14 are operatively attached to balloon 20 and are adapted to move balloon 20 between the first deflated configuration and second inflated configuration. Optionally, the extension tube 13 can be omitted and the inflation device 14 can be operatively attached to the balloon catheter 12. Any inflation device capable of facilitating inflation and deflation of a balloon can be used, and skilled artisans will be able to select a suitable inflation device according to a particular embodiment based on various considerations, including the procedure intended to be performed. Example inflation devices considered suitable include, but are not limited to, manually operated inflation devices, syringes, electromechanical inflation devices, pumps, and any other device considered suitable for a particular application.

In the illustrated embodiment, the extension tube 13 has an extension tube proximal end 15 attached to the measuring device 16 and an extension tube distal end 17 attached to the balloon catheter 12 (e.g., inflation port 26). Thus, the balloon chamber 50 and the measuring device 16 are in fluid communication via a lumen defined by the extension tube 13. Each of the extension tube proximal end 15 and the extension tube distal end 17 can include any suitable connector and/or adapter capable of attaching, or assisting with attaching, one or more devices to the extension tube 13 (e.g., inflation device, measuring device, balloon catheter). Skilled artisans will be able to select a suitable connector and/or adapter to include on an extension tube according to a particular embodiment based on various considerations, including the material(s) that forms the extension tube. Example connectors and/or adapters considered suitable to include on an extension tube include, but are not limited to, threaded connectors, Tuohy Borst adapters, luer lock connectors, and any other connector and/or adapter considered suitable for a particular application.

In the illustrated embodiment, an example of a suitable inflation device 14 is syringe 60 that has a proximal end 62 and a distal end 64 and comprises a barrel 66 and a plunger 68.

Barrel 66 can have any suitable outside diameter and length, and skilled artisans will be able to select a suitable outside diameter and length for a barrel according to a particular embodiment based on various considerations, including the desired amount of fluid intended to be introduced into a balloon chamber. Barrel 66 can be formed of any suitable material, and skilled artisans will be able to select a suitable material to form a barrel according to a particular embodiment based on various considerations, including the type of fluid being introduced into a balloon chamber. Example materials considered suitable to form a barrel include, but are not limited to, biocompatible materials, materials that can be made biocompatible, glasses, polymers, and any other material considered suitable for a particular application.

In the illustrated embodiment, the barrel 66 comprises a barrel proximal end 70, a barrel distal end 72, a barrel length 74, a barrel wall 76, and barrel finger flanges 78. Barrel length 74 extends from the barrel proximal end 70 to the barrel distal end 72. Barrel wall 76 defines a barrel lumen 80, a first barrel opening 82, and a second barrel opening 84. Barrel lumen 80 extends from the first barrel opening 82 to the second barrel opening 84. Each of the barrel finger flanges 78 extends outward and away from the barrel wall 76. Barrel distal end 72 defines barrel threads 86 that are adapted to engage with measuring device 16, as described in more detail herein, to operatively connect, or attach, the syringe 60 to balloon catheter 12.

While a threaded connection between the barrel 66 and the measuring device 16 has been illustrated, any suitable method of attachment between a barrel and a measuring device is considered suitable, and skilled artisans will be able to select a suitable method of attachment between a barrel and a measuring device according to a particular embodiment based on various considerations, including the fluid desired to be introduced into a balloon chamber. Example methods of attachment considered suitable between a barrel and a measuring device include, but are not limited to, threaded connections, luer lock connections, fixed connections, using integrated components, adhesives, tubular members, and any other method of attachment considered suitable for a particular application. For example, a measuring device can be attached to a barrel distal end such that the measuring device is in fluid communication with a fluid being passed through the measuring device. An example structural configuration between an inflation device and a measuring device considered suitable is the configuration provided between the measuring device and inflation device of the Sphere Inflation Device provided by Cook Medical.

Plunger 68 can have any suitable outside diameter and length, and skilled artisans will be able to select a suitable outside diameter and length for a plunger according to a particular embodiment based on various considerations, including the structural arrangement of the barrel of an inflation device. Plunger 68 can be formed of any suitable material, and skilled artisans will be able to select a suitable material to form a plunger according to a particular embodiment based on various considerations, including the type of fluid being introduced into a balloon chamber. Example materials considered suitable to form a plunger include, but are not limited to, biocompatible materials, materials that can be made biocompatible, glasses, polymers, and any other material considered suitable for a particular application.

In the illustrated embodiment, the plunger 68 comprises a plunger proximal end 88, a plunger distal end 90, a plunger length 92, a plunger tip 94, a plunger body 96, and a plunger finger flange 98. Plunger length 92 extends from the plunger proximal end 88 to the plunger distal end 90. Plunger tip 94 is attached to the plunger distal end 90 and is adapted to be received within the barrel lumen 80. In the illustrated embodiment, the plunger 68 is partially disposed within the barrel 66. Plunger finger flange 98 is disposed on the plunger proximal end 88 and extends outward and away from plunger body 96.

Plunger length 92 can be equal to, substantially equal to, greater than, or less than, the barrel length 74. It is considered advantageous for the plunger length 92 to be equal to, substantially equal to, or greater than, the barrel length 74 at least because this configuration advantageously allows for a portion, or the entirety, of a fluid stored within the barrel lumen 80 to pass through the second barrel opening 84 when the barrel distal end 72 is moved toward the plunger tip 94, or vice versa.

Plunger 68 is slidably disposed within the barrel 66 such that the plunger distal end 90 and the plunger tip 94 are each moveable within the barrel lumen 80 along the barrel length 74. Plunger tip 94 is configured to prevent, or substantially prevent, fluid from passing proximally beyond the plunger tip 94 when in use (e.g., when the plunger 68 is disposed within the barrel lumen 80). For example, when a fluid is stored within the barrel lumen 80, such as saline, and the plunger tip 94 and the barrel distal end 72 are moved toward one another, the fluid within the barrel lumen 80 is forced distally through the second barrel opening 84. This can be accomplished by configuring the plunger tip 94 to have an outside diameter that is equal to, substantially equal to, or greater than, the diameter of the barrel lumen 80. Thus, the plunger tip 94 is adapted to provide a moveable sealing engagement with the barrel 66.

Syringe 60 has a first configuration and a second configuration. In the first configuration, the plunger 68 is in a plunger first position such that the plunger tip 94 is disposed proximal to the barrel distal end 72 and the plunger finger flange 98 is disposed proximal to the barrel proximal end 70 a first distance 97 from the barrel proximal end 70. In the first configuration, a fluid can be stored in the barrel lumen 80. In the second configuration, the plunger 68 is in a plunger second position such that the plunger tip 94 is disposed at, adjacent, or near, the barrel distal end 72 and the plunger finger flange 98 is disposed proximal to the barrel proximal end 70 a second distance (not illustrated) from the barrel proximal end 70 that is less than the first distance 97. When the syringe 60 is moved from the first configuration to the second configuration, fluid that is stored within the barrel lumen 80 can be been passed through the barrel lumen 80 and the second barrel opening 84. Thus, when the inflation device 14 is moved from the first configuration to the second configuration, fluid that is stored within the inflation device 14 is introduced into the balloon chamber 50. FIG. 1 illustrates the syringe 60 in the second configuration and FIG. 3 illustrates the syringe 60 in the first configuration. The inclusion of fluid is considered optional, as it may be omitted from the syringe or the inflation devices described herein. When included in an inflation device, the type of fluid will depend on various considerations, and skilled artisans will be able to select a suitable fluid to include in an inflation device according a particular embodiment based on various considerations, including the bodily passage desired to be treated. For example, if a sinus passage, sinus cavity, GI tract, and/or airway is being treated, a fluid such as saline and/or oxygen can be included in an inflation device. Alternatively, if a blood vessel is being treated, a fluid such as saline and/or contrast can be included in an inflation device.

In use, the syringe 60 is attached to the inflation port 26 (e.g., via extension tube, measuring device) and fluid stored within the barrel lumen 80 is introduced into and removed from the balloon chamber 50 by operating the syringe 60 using conventional practices. When the syringe 60 is in the first configuration, the plunger 68 is in the plunger first position and the balloon 20 is in the first deflated configuration. When the syringe 60 is in the second configuration, the plunger 68 is in the plunger second position and the balloon 20 is in the second inflated configuration, or a position between the first deflated configuration and second inflated configuration. Thus, the inflation device 14 (e.g., syringe 60) is operatively connected to the balloon 20 and is adapted to move the balloon 20 between the first deflated configuration and the second inflated configuration.

In the illustrated embodiment, the measuring device 16 is attached to the barrel distal end 72 and the extension tube proximal end 15 using any suitable method of attachment, such as those described herein. Measuring device 16 is in fluid communication with the barrel lumen 80 and the lumen defined by the extension tube 13. Thus, the measuring device 16 is operatively connected, or attached, to the balloon 20 and is in fluid communication with the balloon chamber 50. Measuring device 16 can comprise any suitable device that is adapted to measure the pressure of a fluid contained within a chamber defined by a medical device, such as the balloon chamber 50. Skilled artisans will be able to select a suitable measuring device according to a particular embodiment based on various considerations, including the material(s) that forms a balloon. Example measuring devices considered suitable include, but are not limited to, pressure gauges, mechanical pressure gauges, electromechanical pressure gauges, and any other device considered suitable for a particular application. While the systems, methods, and kits described herein are described as using a mechanical pressure gauge, any suitable measuring device that is adapted to measure the pressure of a fluid disposed within a balloon chamber is considered suitable.

In the illustrated embodiment, the measuring device 16 comprises a measuring device body 102, a plurality of indicia 104, a region 106, and an indicator 108.

Measuring device body 102 defines a measuring device port 110 that is adapted to be operatively connected, or attached, to the inflation port 26 (e.g., via extension tube, inflation device) such that the measuring device 16 is in fluid communication with the inflation lumen 30 and the balloon chamber 50. Alternative to the measuring device 16 being operatively connected, or attached, to the inflation port 26, a measuring device can be operatively connected, or attached, to any suitable portion of a medical system, and skilled artisans will be able to select a suitable portion of a medical system to operatively connect, or attach, a measuring device according to a particular embodiment based on various considerations, including the structural arrangement of a balloon catheter and/or inflation device. For example, alternative to a measuring device being operatively connected, or attached, to an inflation port defined by a balloon catheter, a measuring device can be operatively connected, or attached, to a port defined by an inflation device, or a catheter (e.g., elongate member, inflation port, device port) such that the measuring device is in fluid communication with a chamber defined by a balloon.

Measuring device 16 can be attached to the inflation port 26 using any suitable method of attachment, and skilled artisans will be able to select a suitable method of attachment between a measuring device and an inflation port according to a particular embodiment based on various considerations, including the material(s) that forms the measuring device and/or elongate member. Example methods of attachment considered suitable between a measuring device and an elongate member (e.g., inflation port) include, but are not limited to, threaded connections, luer lock connections, fixed connections, using integrated components (e.g., such that the measuring device is an integrated component with a port, such as an inflation port, defined by an elongate member and is in communication with the chamber defined by a balloon), adhesives, extension tubes, and any other method of attachment considered suitable for a particular application.

Each indicium of the plurality of indicia 104 and the region 106 is disposed on a surface of the measuring device body 102. A first indicium 112 of the plurality of indicia 104 is spaced from a second indicium 114 of the plurality of indicia 104 by a first distance. A third indicium 116 of the plurality of indicia 104 is spaced from the second indicium 114 of the plurality of indicia 104 by a second distance. A fourth indicium 118 of the plurality of indicia 104 is spaced from the third indicia 116 of the plurality of indicia 104 by a third distance. Region 106 extends from a region first end 122 disposed at the fourth indicia 118 of the plurality of indicia 104 to a region second end 124. Thus, region first end 122 is spaced from region second end 124 by the fourth distance. Each indicium of the plurality of indicia 104 and region 106 are printed on the measuring device body 102 using any suitable method, such as using ink on an outer surface of the measuring device body 102.

Each indicium of the plurality of indicia 104 has a form that corresponds to a nominal value of a balloon diameter (e.g., inflated balloon diameter 52). In the illustrated embodiment, the first indicium 112 of the plurality of indicia 104 has a form that corresponds to the nominal value of a first balloon diameter (e.g., zero) when the balloon 20 is in the first deflated configuration and the fluid within the balloon chamber 50 has a first pressure (e.g., zero). The second indicium 114 of the plurality of indicia 104 has a form that corresponds to the nominal value of a second balloon diameter, greater than the first balloon diameter, when the balloon 20 is in the second inflated configuration and the fluid within the balloon chamber 50 has a second pressure that is greater than the first pressure. The third indicium 116 of the plurality of indicia 104 has a form that corresponds to the nominal value of a third balloon diameter, greater than the second balloon diameter, when the balloon 20 is in the second inflated configuration and the fluid within the balloon chamber 50 has a third pressure that is greater than the second pressure. The fourth indicium 118 of the plurality of indicia 104 has a form that corresponds to the nominal value of a fourth balloon diameter, greater than the third balloon diameter and equal to, or substantially equal to, the inflated balloon maximum diameter 54, when the balloon 20 is in the second inflated configuration and the fluid within the balloon chamber 50 has a fourth pressure that is greater than the third pressure. Thus, each indicium of the plurality of indicia 104 expresses a balloon diameter of balloon 20.

Region 106 corresponds to a plurality of nominal values of a balloon diameter along the fourth distance between the region first end 122 and the region second end 124 that extend from the inflated balloon maximum diameter 54 to a diameter that is greater than the inflated balloon maximum diameter 54. The inclusion of the region 106 is considered advantageous at least because it corresponds to a range of balloon diameters that represents the potential failure (e.g., burst, rupture) of a balloon during use. The inclusion of the region 106 is considered optional and in some embodiments it can be omitted.

The form of each indicium of the plurality of indicia can be based on any suitable unit of length, and skilled artisans will be able to select a suitable unit of length to base the form of an indicium according to a particular embodiment based on various considerations, including the material(s) that forms a balloon. Example units of length considered suitable to base the form of an indicium include, but are not limited to, United States customary units, the Metric System, the International System of Units, the French Scale, Imperial units, and any other unit of length considered suitable for a particular application.

Thus, the measuring device 16 is preconfigured such that it is associated with a balloon that has known diameters at particular pressures. This is considered advantageous at least because it provides a mechanism for inflating a balloon to a known diameter without requiring the user to calculate the diameter of the balloon.

While a plurality of indicia 104 and a region 106 have been illustrated, a measuring device can include any suitable number of indicia, plurality of indicia, and/or regions, and skilled artisans will be able to select a suitable number of indicia and regions to include on a measuring device according to a particular embodiment based on various considerations, including the procedure intended to be performed and/or the material(s) that forms a balloon. Example number of indicia, plurality of indicia, and/or regions considered suitable to include on a measuring device include, but are not limited to, zero, one, at least one, two, a plurality, three, four, five, six, and any other number considered suitable for a particular application.

For example, in the illustrated embodiment, the measuring device 16 includes a second plurality of indicia 104'. Each indicium of the second plurality indicia 104' is disposed on a surface of the measuring device body 102. A first indicium 112' of the second plurality of indicia 104' is spaced from a second indicium 114' of the second plurality of indicia 104' by a first distance. A third indicium 116' of the second plurality of indicia 104' is spaced from the second indicium 114' of the second plurality of indicia 104' by a second distance. A fourth indicium 118' of the second plurality of indicia 104' is spaced from the third indicia 116' of the second plurality of indicia 104' by a third distance. Each indicium of the second plurality of indicia 104' is printed on measuring device body 102 using any suitable method, such as using ink on an outer surface of measuring device body 102.

Each indicium of the second plurality of indicia 104' has a form that corresponds to a nominal value of a balloon diameter (e.g., inflated balloon diameter 52). In the illustrated embodiment, the first indicium 112' of the second plurality of indicia 104' has a form that corresponds to the nominal value of a first balloon diameter (e.g., zero) when the balloon 20 is in the first deflated configuration and the fluid within the balloon chamber 50 has a first pressure (e.g., zero). The second indicium 114' of the second plurality of indicia 104' has a form that corresponds to the nominal value of a second balloon diameter, greater than the first balloon diameter, when the balloon 20 is in the second inflated configuration and the fluid within the balloon chamber 50 has a second pressure that is greater than the first pressure. The third indicium 116' of the second plurality of indicia 104' has a form that corresponds to the nominal value of a third balloon diameter, greater than the second balloon diameter, when the balloon 20 is in the second inflated configuration and the fluid within the balloon chamber 50 has a third pressure that is greater than the second pressure. The fourth indicium 118' of the second plurality of indicia 104' has a form that corresponds to the nominal value of a fourth balloon diameter, greater than the third balloon diameter and equal to, or substantially equal to, the inflated balloon maximum diameter 54, when the balloon 20 is in the second inflated configuration and the fluid within the balloon chamber 50 has a fourth pressure that is greater than the third pressure. Thus, each indicium of the second plurality of indicia 104' expresses a balloon diameter of the balloon 20.

While each indicium of the plurality of indicia 104, each indicium of the second plurality of indicia 104', and region 106 have been described as printed on an outer surface of the measuring device body 102, an indicium, plurality of indicia, and/or a region can be printed, defined by, and/or disposed on a measuring device body, or any other portion of a measuring device, using any suitable method. Alternatively, an indicium, plurality of indicia, and/or a region can be printed, defined by, and/or disposed on a separate component that is attached to a measuring device body. Skilled artisans will be able to select a suitable method to print, define, and/or provide an indicium, plurality of indicia, and/or a region on a measuring device body, or another portion of a measuring device, according to a particular embodiment based on various considerations, including the material(s) that forms a measuring device. For example, an indicium, plurality of indicia, and/or region can be embedded within a measuring device body, or a measuring device body can define a protuberance for each indicium and/or region extending outward and away from measuring device body. Alternatively, one or more indicia of a plurality of indicia and/or a region of a measuring device can be formed of a material that has a first color and the measuring device body can be formed of a material that has a second color that is different than the first color.

While each indicium of the plurality of indicia 104 and each indicium of the second plurality of indicia 104' has been illustrated as having a form that corresponds to a nominal value of a balloon diameter, an indicium can have a form that corresponds to any suitable value of a balloon diameter. Skilled artisans will be able to select a suitable value of a balloon diameter for a form of an indicium to correspond to according to a particular embodiment based on various considerations, including the material(s) that forms a balloon. Examples values of a balloon diameter considered suitable for a form of an indicium to correspond to include, but are not limited to, values that are equal to a balloon diameter, substantially equal to a balloon diameter, nominal values of a balloon diameter, and any other value considered suitable for a particular application.

Figure 4:
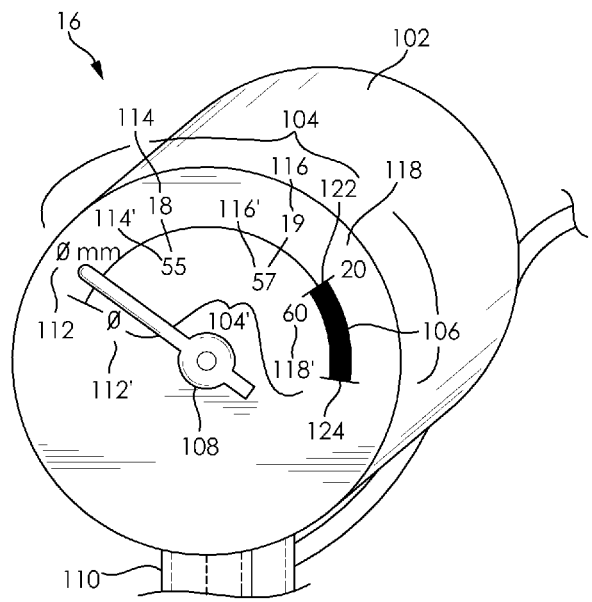
FIG. 4 is a magnified view of area 4 indicated in FIG. 1 showing the indicator in an indicator first position.
Figure 4A:
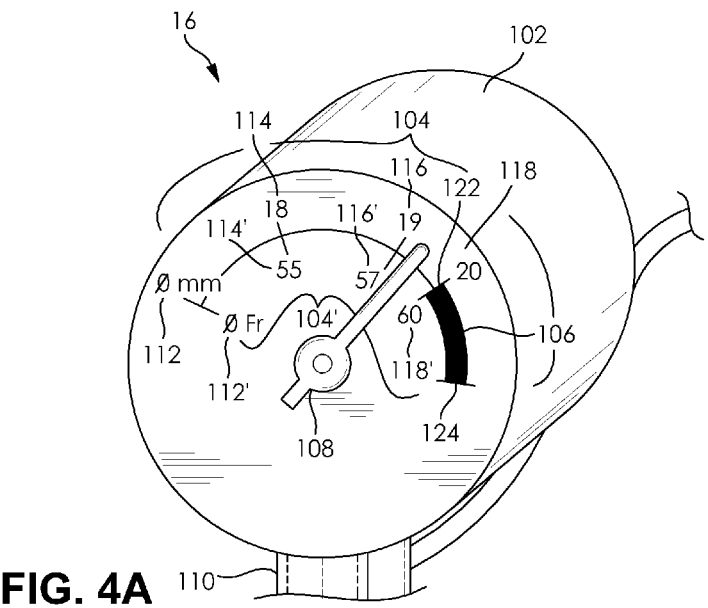
FIG. 4A is a magnified view of area 4 indicated in FIG. 1 showing the indicator in an indicator second position.

Indicator 108 is operatively attached to the measuring device 16 such that it is moveable on the measuring device body 102 between an indicator first position, illustrated in FIG. 4, to an indicator second position, illustrated in FIG. 4A. Indicator 108 moves from the indicator first position to the indicator second position when the measuring device 16 detects an increase in the pressure in the fluid within the balloon chamber 50, such as when a fluid is introduced into balloon chamber 50. Indicator 108 is disposed on the measuring device body 102 such that movement of the indicator 108 from the indicator first position to the indicator second position is accomplished relative to the plurality of indicia 104, the second plurality of indicia 104', and/or the region 106. Movement of the indicator 108 can be accomplished using any suitable structural configuration within a measuring device 16, and skilled artisans will be able to select a suitable structural configuration to accomplish movement of an indicator according to a particular embodiment based on various considerations, including the type of procedure intended to be completed. For example, a measuring device can include a Bourbon tube operatively connected, or attached, to an indicator to effectuate movement of the indicator when a pressure is applied to the measuring device or the fluid within a balloon chamber.

When the indicator 108 is in the indicator first position, the balloon 20 is in the first deflated configuration and the fluid within the balloon chamber 50 has a first pressure (e.g., zero). In the indicator first position, the indicator 108 is positioned relative to an indicium of the plurality of indicia 104 and an indicium of the second plurality of indicia 104' that corresponds to the balloon diameter (e.g., zero). When the indicator 108 is in the indicator second position, the balloon 20 is in the second inflated configuration and the fluid within the balloon chamber 50 has a second pressure that is greater than the first pressure. In the indicator second position, the indicator 108 is positioned relative to an indicium of the plurality of indicia 104 and an indicium of the second plurality of indicia 104' that corresponds to the inflated balloon diameter. Thus, as the inflation device 14 moves from the first configuration toward the second configuration (e.g., plunger moves from the first position toward the second position) and the pressure of the fluid within the balloon chamber 50 increases, the indicator 108 moves relative to the plurality of indicia 104 and the second plurality of indicia 104' in a direction that corresponds to an increase in the diameter of the balloon 20. Alternatively, as the inflation device 14 moves from the second configuration toward the first configuration and the pressure of the fluid within the balloon chamber 50 decreases, the indicator 108 moves relative to the plurality of indicia 104 and the second plurality of indicia 104' in a direction that corresponds to a decrease in the diameter of the balloon 20. The distance the indicator 108 moves from the indicator first position to the indicator second position, or vice versa, is relative to the increase or decrease of the pressure of the fluid within the balloon chamber 50.

While an indicator 108 that is moveable on measuring device 12 has been illustrated, a measuring device can include any suitable indicator, and skilled artisans will be able to select a suitable indicator to include on a measuring device according to a particular embodiment based on various considerations, including the procedure desired to be completed. Example indicators considered suitable to include on a measuring device include, but are not limited to, indicators that are mechanically attached to a measuring device, indicators that are electronically attached to a measuring device, electronic indicators, and any other indicator considered suitable for a particular application.

While a particular structural configuration has been illustrated for the measuring device 16, a measuring device can have any suitable structural configuration and skilled artisans will be able to select a suitable structural configuration for a measuring device according to a particular embodiment based on various considerations, including the structural configuration of a balloon.

In use, as the inflation device 14 is moved from the first configuration toward the second configuration, fluid is introduced into the balloon chamber 50 and becomes pressurized. Measuring device 16 detects the increase in pressure of the fluid within the balloon chamber 50, which results in movement of the indicator 108 from its indicator first position to its indicator second position. As discussed herein, the distance the indicator 108 moves between the indicator first position and the indicator second position is relative to the increase or decrease in the pressure of the fluid within the balloon chamber 50. When the indicator 108 is in the indicator second position, it is positioned relative to an indicium of the plurality of indicia 104 and an indicium of the second plurality of indicia 104' that corresponds to the diameter of the balloon 20 (e.g., inflated balloon diameter 52). This is considered advantageous at least because it reduces the potential for a user inflating a balloon to an incorrect diameter and/or causing the balloon to burst by exceeding a balloon maximum diameter.

As a result of the material that forms a balloon and the structural configuration of the balloon influencing the pressure required to move the balloon from a first deflated configuration to a second inflated configuration, each different model balloon will require the application of different pressures to achieve a particular inflated balloon diameter. Thus, a measuring device can be preconfigured such that each indicium, indicium of a plurality of indicium, and/or region has a form that corresponds to the nominal value of a balloon diameter of a particular balloon in the first deflated configuration and/or second inflated configuration.

While the measuring device 16 has been illustrated as a separate component attached to an inflation device 14, any structural arrangement that provides fluid communication between a measuring device and a balloon chamber is considered suitable. Skilled artisans will be able to select a suitable structural arrangement for a particular embodiment based on various considerations, including the structural arrangement of an inflation device and/or balloon catheter. An example structural arrangement considered suitable includes, but is not limited to, attaching a measuring device between a proximal inflation port end and a distal inflation port end such that the measuring device is disposed along the length of the inflation port and in fluid communication with the inflation port lumen. A measuring device can be disposed on any portion, part, or feature of an inflation device, extension tube, or balloon catheter, such as those portions, parts, or features described herein.

Figure 5:
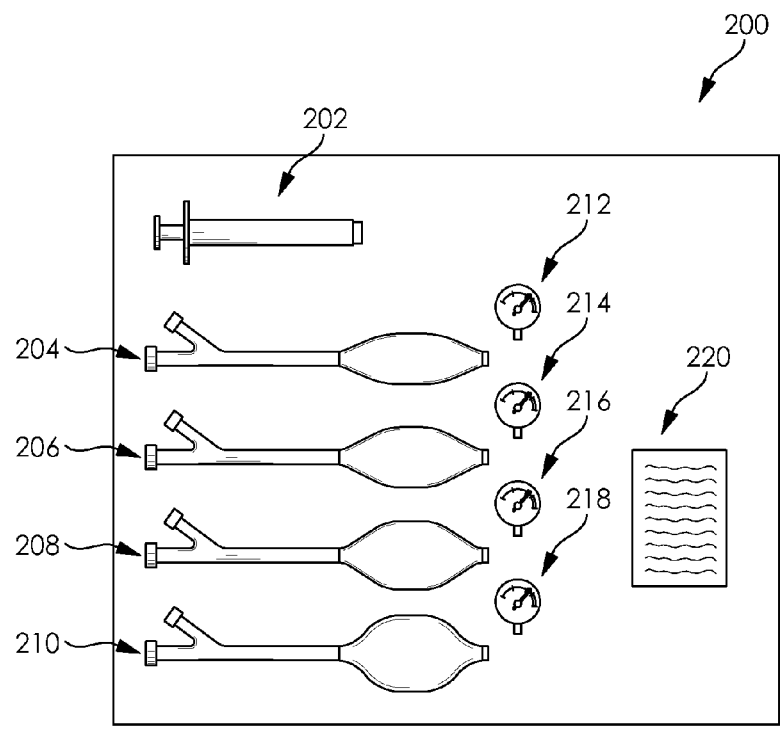
FIG. 5 illustrates an exemplary kit.

FIG. 5 illustrates an exemplary kit 200 that comprises an inflation device 202, a first balloon catheter 204, a second balloon catheter 206, a third balloon catheter 208, a fourth balloon catheter 210, a first measuring device 212, a second measuring device 214, a third measuring device 216, a fourth measuring device 218, and instructions for use 220.

Inflation device 202 can comprise any suitable device that is adapted to move a balloon from a first deflated configuration to a second inflated configuration, such as inflation device 14.

Each of the first balloon catheter 204, the second balloon catheter 206, the third balloon catheter 208, and the fourth balloon catheter 210 can have any suitable structural configuration, such as balloon catheter 12. In the illustrated embodiment, the first balloon catheter 204 has a first balloon configuration, the second balloon catheter 206 has a second balloon configuration, the third balloon catheter 208 has a third balloon configuration, and the fourth balloon catheter 210 has a fourth balloon configuration. The first balloon configuration has a first balloon maximum diameter. The second balloon configuration has a second balloon maximum diameter that is different than the first balloon maximum diameter. The third balloon configuration has a third balloon maximum diameter that is different than the second balloon maximum diameter and first balloon maximum diameter. The fourth balloon has a fourth balloon maximum diameter that is different than the third balloon maximum diameter, the second balloon maximum diameter, and the first balloon maximum diameter. It is considered advantageous to include a plurality of balloon catheters where at least one of the balloon catheters has a different maximum diameter and/or balloon configuration from a second balloon catheter at least because this provides a mechanism for selecting an appropriate balloon catheter to accomplish a procedure.

While a first balloon catheter 204, a second balloon catheter 206, a third balloon catheter 208, and a fourth balloon catheter 210 have been illustrated, any suitable number of balloon catheters that have any suitable structural configuration can be included in a kit. Skilled artisans will be able to select a suitable number of balloon catheters to include in a kit and a suitable structural configuration for each balloon catheter according to a particular embodiment based on various considerations, including the procedure intended to be performed. Example number of balloon catheters considered suitable to include in a kit include, but are not limited to, one, at least one, two, a plurality, three, four, five, six, seven, eight, and any other number considered suitable for a particular application.

Each of the first measuring device 212, the second measuring device 214, the third measuring device 216, and the fourth measuring device 218 can have any suitable structural configuration, such as the measuring device 16. In the illustrated embodiment, the first measuring device 212 is preconfigured such that each indicium of the plurality of indicia included on first measuring device 212 has a form that corresponds to the nominal value of a balloon diameter at a particular pressure of the balloon included on the first balloon catheter 204. Second measuring device 214 is preconfigured such that each indicium of the plurality of indicia included on the second measuring device 214 has a form that corresponds to the nominal value of a balloon diameter at a particular pressure of the balloon included on second balloon catheter 206. Third measuring device 216 is preconfigured such that each indicium of the plurality of indicia included on the third measuring device 216 has a form that corresponds to the nominal value of a balloon diameter at a particular pressure of the balloon included on the third balloon catheter 208. Fourth measuring device 218 is preconfigured such that each indicium of the plurality of indicia included on the fourth measuring device 218 has a form that corresponds to the nominal value of a balloon diameter at a particular pressure of the balloon included on the fourth balloon catheter 210. It is considered advantageous for a measuring device to be preconfigured, or associated with, a particular balloon catheter at least because this configuration provides a mechanism for providing a diameter of the balloon included on the balloon catheter when it is in use (e.g., in an inflated configuration).

While a first measuring device 212, a second measuring device 214, a third measuring device 216, and a fourth measuring device 218 have been illustrated, any suitable number of measuring devices that have any suitable structural configuration can be included in a kit. Skilled artisans will be able to select a suitable number of measuring devices to include in a kit and a suitable structural configuration for each measuring device according to a particular embodiment based on various considerations, including the procedure intended to be performed. Example number of measuring devices considered suitable to include in a kit include, but are not limited to, one, at least one, two, a plurality, three, four, five, six, seven, eight, and any other number considered suitable for a particular application. Alternatively, a measuring device can be provided separate from a balloon catheter and/or inflation device. Optionally, the instructions for use 220 can be omitted from kit 200.

Figure 6:
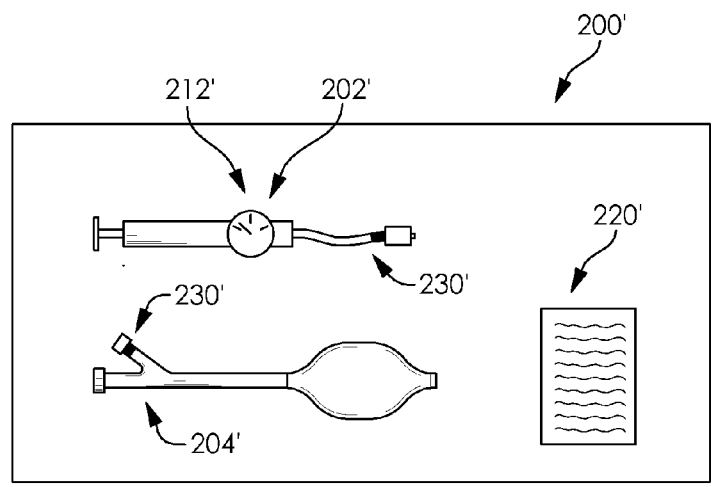
FIG. 6 illustrates another exemplary kit.

FIG. 6 illustrates another exemplary kit 200' that comprises an inflation device 202', a balloon catheter 204', a measuring device 212', and instructions for use 220'. Balloon catheter 204' can have any suitable structural configuration, such as balloon catheter 12. In the illustrated embodiment, balloon catheter 204' has a balloon maximum diameter.

Inflation device 202' can comprise any suitable device that is adapted to move a balloon from a first deflated configuration to a second inflated configuration, such as inflation device 14. In the illustrated embodiment, the measuring device 212' is attached to the inflation device 202' such that the measuring device 212' is in fluid communication with the barrel lumen of the inflation device 202'. Measuring device 212' can have any suitable structural configuration, such as measuring device 16. In the illustrated embodiment, the measuring device 212' is preconfigured such that each indicium of the plurality of indicia included on the measuring device 212 has a form that corresponds to the nominal value of a balloon diameter at a particular pressure of the balloon included on the balloon catheter 204'.

In the illustrated embodiment, the inflation device 202' (e.g., barrel, plunger, extension tube, inflation device, measuring device) and the balloon catheter 204' (e.g., elongate member, balloon) each include an indicium 230' printed on an outer surface of the component that provides a mechanism for matching a preconfigured measuring device to a balloon catheter.

While the indicia 230' have been described as printed on an outer surface of the inflation device 202' and the balloon catheter 204', an indicium can be printed, defined by, and/or disposed on an inflation device, measuring device, and/or balloon catheter at any suitable location and using any suitable method. Alternatively, an indicium can be printed, defined by, and/or disposed on a separate component that is attached to an inflation device and/or balloon catheter. Skilled artisans will be able to select a suitable method to print, define, and/or provide an indicium on an inflation device, measuring device, and/or balloon catheter according to a particular embodiment based on various considerations, including the material(s) that forms an inflation device, measuring device, and/or balloon catheter. Optionally, an indicium disposed on an inflation device, measuring device, and/or balloon catheter can be color coded such that preconfigured measuring devices are matched to a desired balloon catheter. Any suitable color can be used including, but not limited to, red, green, black, blue, and any other color considered suitable for a particular application.

Optionally, an inflation device (e.g., barrel distal end, extension tube, measuring device) and a balloon catheter (e.g., inflation port) and/or balloon catheter (e.g., port, inflation port) can have one or more fittings (e.g., custom fittings) that are configured such that only measuring devices that are preconfigured for the balloon catheter can be utilized with a particular inflation device and/or balloon catheter.

Various methods of treatment are provided herein. While the methods described herein are shown and described as a series of acts, it is to be understood and appreciated that the methods are not limited by the order of acts, as some acts may, in accordance with these methods, occur in different orders with other acts described herein, and/or concurrently with other acts described herein.

Figure 7:
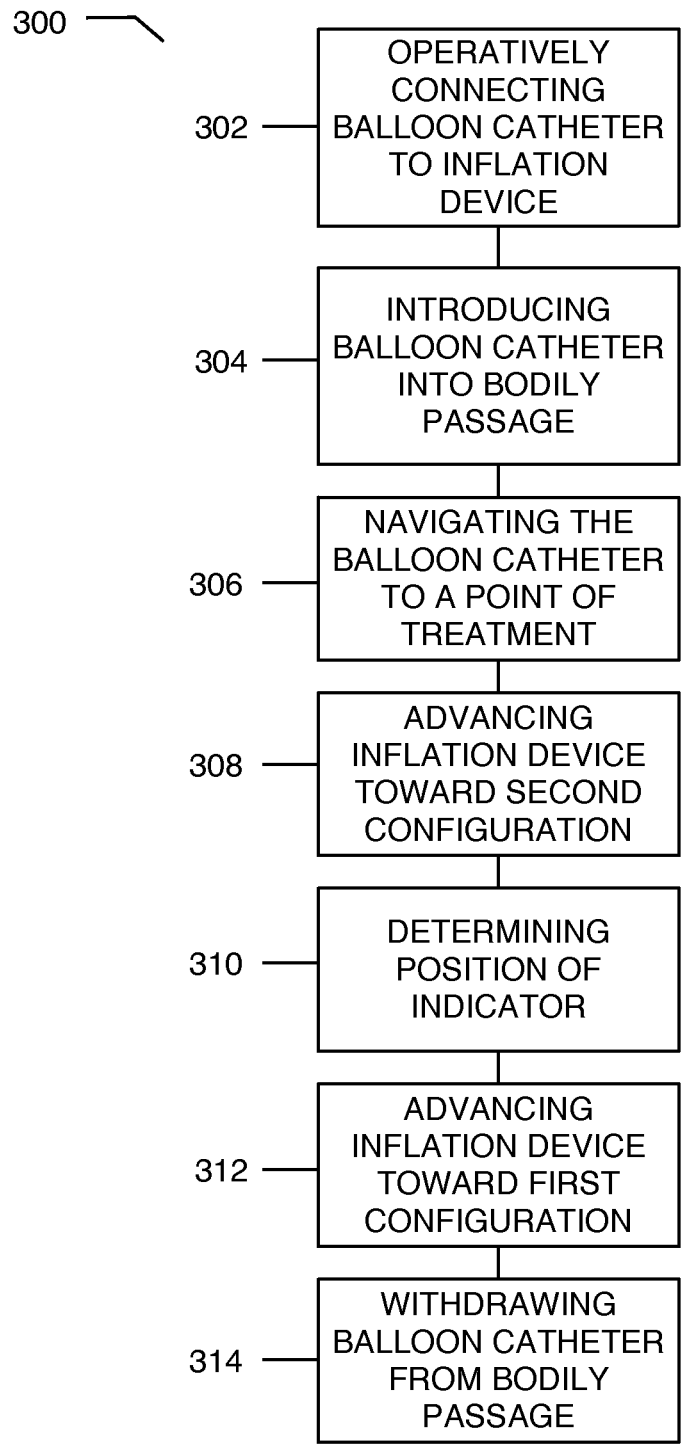
FIG. 7 is a flowchart representation of an exemplary method of treatment.

FIG. 7 is a flowchart representation of an exemplary method of treatment 300.

A step 302 comprises operatively connecting a balloon catheter that has an elongate member and a balloon that defines a balloon chamber to an inflation device. The balloon catheter has a balloon catheter proximal end and a balloon catheter distal end. The balloon is moveable between a first deflated configuration and a second inflated configuration as fluid moves into and out of the balloon chamber. The balloon has an inflated balloon diameter in the second inflated configuration. The inflation device is adapted to move between a first configuration and a second configuration such that movement of the inflation device from the first configuration toward the second configuration results in fluid being introduced into the balloon chamber moving the balloon from the first deflated configuration to the second inflated configuration. A measuring device is attached to the inflation device (e.g., barrel distal end) such that it is operatively connected to the balloon catheter and is in fluid communication with the balloon chamber. Alternatively, the measuring device can be a component of the balloon catheter (e.g., be mounted on a port define by the balloon catheter and in fluid communication with the chamber defined by the balloon). The measuring device is adapted to measure the pressure of the fluid disposed within the balloon chamber and has a measuring device body, a plurality of indicia disposed on the measuring device body, and an indicator. Each indicium of the plurality of indicia has a form that corresponds to the nominal value of a balloon diameter. The indicator is moveable on the measuring device relative to the plurality of indicia and between an indicator first position when the balloon is in the first deflated configuration and the fluid within the balloon chamber has a first pressure and an indicator second position when the balloon is in the second inflated configuration and the fluid within the balloon chamber has a second pressure. The second pressure is greater than the first pressure. In the indicator second position, the indicator is positioned relative to an indicium of the plurality of indicia that corresponds to the inflated balloon diameter. Another step 304 comprises introducing the balloon catheter distal end into a bodily passage such that the balloon catheter distal end is disposed within the bodily passage. Another step 306 comprises navigating the balloon catheter distal end to a point of treatment within the bodily passage. Another step 308 comprises advancing the inflation device from the inflation device first configuration toward the inflation device second configuration such that the balloon moves from the first deflated configuration to the second inflated configuration. Another step 310 comprises determining the position of the indicator relative to an indicium of the plurality of indicia when in the indicator is in the indicator second position. Another step 312 comprises advancing the inflation device from the inflation device second configuration toward the inflation device first configuration, or proximal to the inflation device first configuration, such that the balloon moves from the second inflated configuration toward the first deflated configuration. Another step 314 comprises withdrawing the balloon catheter distal end from the bodily passage.

Step 302 can be accomplished using any suitable balloon catheter and any suitable inflation device, such as those described herein. Attachment between a balloon catheter and an inflation device can be accomplished using any suitable method of attachment, such as threaded connections. Optionally, this step can be omitted and an inflation device can be an integral component of a balloon catheter, or pre-attached to a balloon catheter. Attachment between a measuring device and a balloon catheter and/or inflation device can be accomplished using any suitable method of attachment, such as threaded connections, and using any suitable measuring device, such as those described herein. Optionally, a measuring device can be an integral component of, or pre-attached to, a balloon catheter and/or inflation device.

Step 304 can be accomplished by locating the bodily passage within which it is desired to introduce the balloon catheter and placing a distally-directed force on any suitable portion of the balloon catheter such that the balloon catheter distal end is passed through an opening of the bodily passage and disposed within the bodily passage.

Step 306 can be accomplished by continuing to apply a distally-directed force on any suitable portion of the balloon catheter and by using direct visualization or any other suitable method of visualizing a medical device within a bodily passage during a procedure. For example, x-ray, fluoroscopy, transcutaneous visualization, and using a camera disposed on the balloon catheter, or provided separately, are considered suitable methods of visualizing the position of a medical device within a bodily passage during a procedure.

Step 308 can be accomplished by advancing inflation device from its inflation device first configuration toward its inflation device second configuration. For example, if the inflation device is a syringe, such as syringe 60, step 310 can be accomplished by placing a distally-directed force on a plunger such that plunger is moved from the plunger first position toward the plunger second position and fluid disposed within the barrel lumen is introduced into the balloon chamber.

Step 310 can be accomplished by direct visualization of the position of indicator relative to an indicium of the plurality of indicia disposed on a measuring device that has a form that corresponds to the nominal value of a balloon diameter. This is considered advantageous at least because it allows a user to ascertain the diameter of the balloon during treatment without the use of a scope or having to calculate the diameter.

An optional step comprises determining whether the position of the indicator in the indicator second position is relative to an indicium of the plurality of indicia that corresponds to a desired predetermined inflated balloon diameter. This optional step can be accomplished by direct visualization of the position of the indicator in the indicator second position relative to an indicium of the plurality of indicia or a region disposed on a measuring device. The desired predetermined inflated balloon diameter can be based on the structural arrangement of a bodily passage (e.g., sinus passage, airway, sinus cavity, vessel, GI tract), a feature of a bodily passage, the procedure intended to be performed, the structural arrangement of a device intended to be positioned in a bodily passage subsequent to dilation, or a predetermined diameter. For example, the desired predetermined inflated balloon diameter can be based on a known characteristic of a bodily passage (e.g., normal diameter of bodily passage). Another optional step comprises determining a desired inflated balloon diameter based on a feature of a bodily passage.

Step 312 can be accomplished by advancing inflation device from the inflation device second configuration toward the inflation device first configuration, and/or proximal of the inflation device first configuration such that negative pressure is generated. For example, if the inflation device is a syringe, such as syringe 60, step 314 can be accomplished by placing a proximally-directed force on a plunger such that the plunger is moved from the plunger second position toward the plunger first position and fluid within the balloon chamber is withdrawn into the barrel lumen.

Step 314 can be accomplished by placing a proximally-directed force on any suitable portion of the balloon catheter such that the balloon catheter distal end is withdrawn from the bodily passage.

An optional step comprises repeating the step of determining the position of the indicator relative to an indicium of the plurality of indicia in the indicator second position subsequent to completing the step of advancing the inflation device from the second configuration toward the first configuration such that fluid is removed from the balloon chamber. Another optional step comprises repeating the step of moving the inflation device from the inflation device first configuration toward the inflation device second configuration such that fluid is introduced into the balloon chamber and the balloon is moved from a configuration between the first deflated configuration and the second inflated configuration to its second inflated configuration. Another optional step comprises repeating the step of determining the position of the indicator relative to an indicium of the plurality of indicia in the indicator second position subsequent to repeating the step of advancing the inflation device from the inflation device first configuration to the inflation device second configuration. Another optional step comprises continuing the advancement of the inflation device toward the inflation device second configuration such that additional fluid is introduced into the balloon chamber and until the position of the indicator in the indicator second position is relative to an indicium of the plurality of indicia that corresponds to a desired and/or predetermined inflated balloon diameter.

While various steps, alternatives steps, and optional steps have been described above with respect to method of treatment 300, these steps, alternative steps, and optional steps can be included in, accomplished concurrently with, and/or accomplished in the alternative to, the methods, steps, alternative steps, and/or optional steps described below with respect to exemplary method 400.

Figure 8:
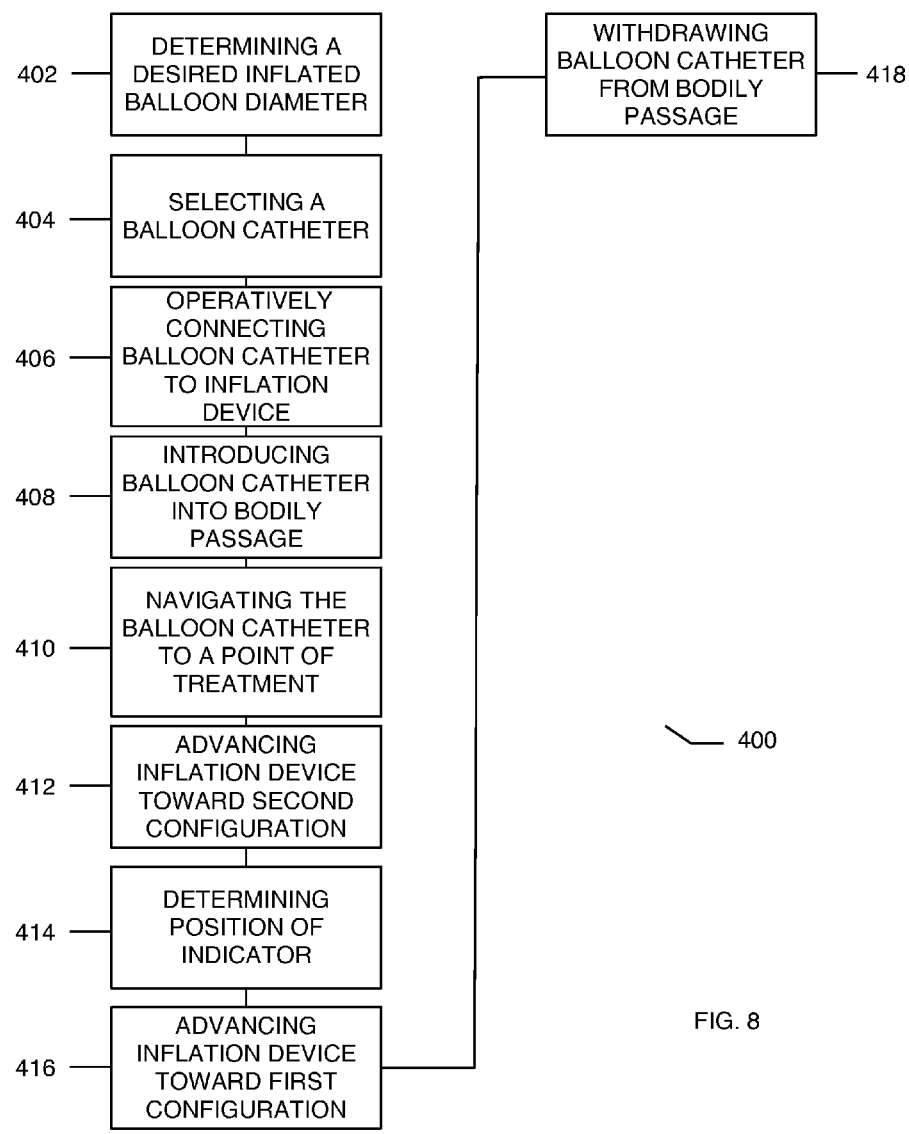
FIG. 8 is a flowchart representation of another exemplary method of treatment.

FIG. 8 is a flowchart representation of another exemplary method of treatment 400.

A step 402 comprises determining a desired inflated balloon diameter to inflate a balloon. Another step 404 comprises selecting a balloon catheter that has an elongate member and a balloon that defines a balloon chamber. The balloon catheter has a balloon catheter proximal end and a balloon catheter distal end. The balloon is moveable between a first deflated configuration and a second inflated configuration as fluid moves into and out of the balloon chamber. The balloon has an inflated balloon diameter in the second inflated configuration. Another step 406 comprises operatively connecting the balloon catheter to an inflation device. The inflation device is adapted to move between a first configuration and a second configuration. Movement of the inflation device from the first configuration to the second configuration results in fluid being introduced into the balloon chamber moving the balloon from the first deflated configuration to the second inflated configuration. A measuring device is attached to the inflation device (e.g., barrel distal end) such that it is operatively connected to the balloon catheter and is in fluid communication with the balloon chamber. Alternatively, the measuring device can be a component of the balloon catheter (e.g., be mounted on a port define by the balloon catheter and in fluid communication with the chamber defined by the balloon). The measuring device is adapted to measure the pressure of the fluid disposed within the balloon chamber and has a measuring device body, a plurality of indicia disposed on the measuring device body, and an indicator. Each indicium of the plurality of indicia has a form that corresponds to the nominal value of a balloon diameter. The indicator is moveable on the measuring device relative to the plurality of indicia and between an indicator first position when the balloon is in the first deflated configuration and the fluid within the balloon chamber has a first pressure and an indicator second position when the balloon is in the second inflated configuration and the fluid within the balloon chamber has a second pressure. The second pressure is greater than the first pressure. In the indicator second position, the indicator is positioned relative to an indicium of the plurality of indicia that corresponds to the inflated balloon diameter. Another step 408 comprises introducing the balloon catheter distal end into a bodily passage such that the balloon catheter distal end is disposed within the bodily passage. Another step 410 comprises navigating the balloon catheter distal end to a point of treatment within the bodily passage. Another step 412 comprises advancing the inflation device from the inflation device first configuration toward the inflation device second configuration such that the balloon moves from the first deflated configuration to the second inflated configuration. Another step 414 comprises determining the position of the indicator relative to an indicium of the plurality of indicia when the indicator is in the indicator second position. Another step 416 comprises advancing the inflation device from the inflation device second configuration toward the inflation device first configuration, or proximal to the inflation device first configuration, such that the balloon moves from the second inflated configuration toward the first deflated configuration. Another step 418 comprises withdrawing the balloon catheter distal end from the bodily passage.

Step 402 can be accomplished based on the structural arrangement of a bodily passage (e.g., sinus passage, airway, sinus cavity, vessel, GI tract), the procedure intended to be performed, the structural arrangement of a device intended to be positioned in a bodily passage subsequent to dilation, or a predetermined diameter. For example, this step can be accomplished based on a known characteristic of a bodily passage (e.g., normal diameter of bodily passage) or a feature of a bodily passage (e.g., natural diameter of an ostium).

Step 404 can be accomplished based on the diameter selected in step 402. For example, this step can be accomplished by selecting a balloon catheter that has, or is capable of achieving, an inflated balloon diameter equal to, substantially equal to, greater than, or less than, the desired inflated balloon diameter. Optionally, a kit, such as kit 200, can be provided and this step can comprise selecting a balloon catheter from a plurality of balloon catheters that can achieve the diameter selected in step 402. Optionally, the balloon catheter can include an attached measuring device, such as those described herein (e.g., attached to a port defined by the elongate member).

Step 406 is accomplished as described above with respect to step 302 and can be accomplished based on the balloon catheter selected in the step of selecting a balloon catheter (e.g., the balloon catheter that is intended to be used to dilate the bodily passage). For example, this step can be accomplished by selecting an inflation device that includes a measuring device that is preconfigured to provide a diameter of the balloon included on the balloon catheter selected in step 404. Thus, the selected measuring device has a plurality of indicia such that each indicium of the plurality of indicia has a form that corresponds to a balloon diameter of the selected balloon. Optionally, the inflation device can omit the inclusion of a measuring device in embodiment in which the balloon catheter includes an attached measuring device. Optionally, a kit, such as kit 200, can be provided and this step can comprise selecting a measuring device from a plurality of measuring devices.

Step 408 is accomplished as described above with respect to step 304. Step 410 is accomplished as described above with respect to step 306. Step 412 is accomplished as described above with respect to step 308. Step 414 is accomplished as described above with respect to step 310. Step 416 is accomplished as described above with respect to step 312. Step 418 is accomplished as described above with respect to step 314.

While various steps, alternatives steps, and optional steps have been described above with respect to method of treatment 400, these steps, alternative steps, and optional steps can be included in, accomplished concurrently with, and/or accomplished in the alternative to, the methods, steps, alternative steps, and/or optional steps described above with respect to exemplary method 300.

Any of the medical systems, methods, steps, alternative steps, optional steps, and kits described herein can be used to perform a procedure and/or provide treatment within any suitable bodily passage, and skilled artisans will be able to select a suitable bodily passage to use a medical system, method, and/or kit according to a particular embodiment based on various considerations, such as the procedure and/or treatment intended to be performed. Example bodily passages within which a medical system, method, and/or kit, such as those described herein, can be used include, but are not limited to, sinus passages, airways, sinus cavities, body vessels, salivary ducts, the urinary tract, the GI tract, and any other bodily passage considered suitable for a particular application.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A method for treating a bodily passage, the method comprising the steps of:
operatively connecting a balloon catheter having an elongate member and a balloon that defines a balloon chamber to an inflation device, the balloon catheter having a balloon catheter proximal end and a balloon catheter distal end, the balloon moveable between a first deflated configuration and a second inflated configuration as fluid moves into and out of the balloon chamber, the balloon having an inflated balloon diameter in the second inflated configuration, the inflation device adapted to move the balloon between the first deflated configuration and the second inflated configuration, the inflation device moveable between an inflation device first configuration and an inflation device second configuration such that when the inflation device is in the inflation device first configuration the balloon is in the first deflated configuration and when the inflation device is in the inflation device second configuration the balloon is in the second inflated configuration;
operatively connecting a measuring device to the balloon catheter such that the measuring device is in fluid communication with the balloon chamber, the measuring device adapted to measure the pressure of the fluid disposed within the balloon chamber and having a measuring device body, a plurality of indicia disposed on the measuring device body, and an indicator, each indicium of the plurality of indicia has a form that corresponds to a nominal value of a balloon diameter, the indicator operatively attached to the measuring device such that the indicator is moveable on the measuring device relative to the plurality of indicia and between an indicator first position when the balloon is in the first deflated configuration and the fluid within the balloon chamber has a first pressure and an indicator second position when the balloon is in the second inflated configuration and the fluid within the balloon chamber has a second pressure, the second pressure being greater than the first pressure, in the indicator second position the indicator is positioned relative to an indicium of the plurality of indicia that corresponds to the inflated balloon diameter;
introducing the balloon catheter distal end into said bodily passage such that the balloon catheter distal end is disposed within said bodily passage;
navigating the balloon catheter distal end to a point of treatment within said bodily passage;
advancing the inflation device from the inflation device first configuration toward the inflation device second configuration such that the balloon moves from the first deflated configuration toward the second inflated configuration;
determining the position of the indicator in the indicator second position relative to the plurality of indicia;
advancing the inflation device from the inflation device second configuration toward the inflation device first configuration such that the balloon moves from the second inflated configuration toward the first deflated configuration; and
withdrawing the balloon catheter distal end from said bodily passage;
wherein the entire measuring device is disposed outside of the balloon chamber.

2. The method of claim 1, further comprising the step of determining if the position of the indicator in the indicator second position is relative to an indicium of the plurality of indicia that corresponds to a predetermined inflated balloon diameter.

3. The method of claim 1, further comprising the step of advancing the inflation device toward the inflation device second configuration until the position of the indicator in the indicator second position is relative to an indicium of the plurality of indicia that corresponds to a predetermined inflated balloon diameter.

4. The method of claim 3, wherein the predetermined inflated balloon diameter is based on a feature of said bodily passage.

5. A medical system comprising:
a balloon having a balloon wall defining a balloon chamber, the balloon moveable between a first deflated configuration and a second inflated configuration as a fluid moves into and out of the balloon chamber, the balloon having an inflated balloon diameter in the second inflated configuration;
an inflation device operatively connected to the balloon and adapted to move the balloon between the first deflated configuration and the second inflated configuration; and
a measuring device operatively connected to the balloon and in fluid communication with the balloon chamber, the measuring device adapted to measure the pressure of the fluid disposed within the balloon chamber and having a measuring device body, a plurality of indicia disposed on the measuring device body, and an indicator, the indicator operatively attached to the measuring device such that the indicator is moveable on the measuring device relative to the plurality of indicia and between an indicator first position when the balloon is in the first deflated configuration and the fluid within the balloon chamber has a first pressure and an indicator second position when the balloon is in the second inflated configuration and the fluid within the balloon chamber has a second pressure, the second pressure being greater than the first pressure;
wherein in the indicator second position the indicator is positioned relative to an indicium of the plurality of indicia that corresponds to the inflated balloon diameter;
wherein the entire measuring device is disposed outside of the balloon chamber.

6. The medical system of claim 5, wherein each indicium of the plurality of indicia has a form that corresponds to a nominal value of a balloon diameter.

7. The medical system of claim 6, wherein a first indicium of the plurality of indicia has a form that corresponds to the nominal value of a first balloon diameter; and
wherein a second indicium of the plurality of indicia has a form that corresponds to the nominal value of a second balloon diameter, the second balloon diameter being greater than the first balloon diameter.

8. The medical system of claim 6, wherein the measuring device has a second plurality of indicia; and
wherein each indicium of the second plurality of indicia has a form that corresponds to a nominal value of a balloon diameter.

9. The medical system of claim 5, wherein the balloon has an inflated balloon maximum diameter; and wherein an indicium of the plurality of indicia has a form that corresponds to a nominal value of the inflated balloon maximum diameter.

10. The medical system of claim 9, wherein the measuring device has a region that extends from a region first end to a region second end, the region first end disposed at the indicium of the plurality of indicia that has a form that corresponds to the nominal value of the inflated balloon maximum diameter.

11. The medical system of claim 5, wherein the inflation device comprises a barrel and a plunger, the plunger slidably disposed within the barrel and moveable between a plunger first position and a plunger second position; and wherein movement of the plunger from the plunger first position to the plunger second position moves the balloon from the first deflated configuration to the second inflated configuration.

12. The medical system of claim 5, wherein the measuring device is attached to the inflation device.

13. The medical system of claim 5, further comprising an elongate member defining an inflation lumen;

wherein the balloon is attached to the elongate member such that the balloon chamber is in fluid communication with the inflation lumen.

14. A medical system comprising:

a balloon having a balloon wall defining a balloon chamber, the balloon moveable between a first deflated configuration and a second inflated configuration as a fluid moves into and out of the balloon chamber, the balloon having an inflated balloon diameter in the second inflated configuration;

an inflation device operatively connected to the balloon and adapted to move the balloon between the first deflated configuration and the second inflated configuration; and a measuring device operatively connected to the balloon and in fluid communication with the balloon chamber, the measuring device adapted to measure the pressure of the fluid disposed within the balloon chamber and having a measuring device body, a plurality of indicia disposed on the measuring device body, and an indicator, the indicator operatively attached to the measuring device such that the indicator is moveable on the measuring device relative to the plurality of indicia and between an indicator first position when the balloon is in the first deflated configuration and the fluid within the balloon chamber has a first pressure and an indicator second position when the balloon is in the second inflated configuration and the fluid within the balloon chamber has a second pressure, the second pressure being greater than the first pressure;

wherein in the indicator second position the indicator is positioned relative to an indicium of the plurality of indicia that corresponds to the inflated balloon diameter; and wherein the measuring device is a pressure gauge.

15. The medical system of claim 14, wherein each indicium of the plurality of indicia has a form that corresponds to a nominal value of a balloon diameter.

16. The medical system of claim 15, wherein a first indicium of the plurality of indicia has a form that corresponds to the nominal value of a first balloon diameter; and wherein a second indicium of the plurality of indicia has a form that corresponds to the nominal value of a second balloon diameter, the second balloon diameter being greater than the first balloon diameter.

17. The medical system of claim 15, wherein the measuring device has a second plurality of indicia; and wherein each indicium of the second plurality of indicia has a form that corresponds to a nominal value of a balloon diameter.

18. The medical system of claim 14, wherein the balloon has an inflated balloon maximum diameter; and wherein an indicium of the plurality of indicia has a form that corresponds to a nominal value of the inflated balloon maximum diameter.

19. The medical system of claim 18, wherein the measuring device has a region that extends from a region first end to a region second end, the region first end disposed at the indicium of the plurality of indicia that has a form that corresponds to the nominal value of the inflated balloon maximum diameter.

20. The medical system of claim 14, wherein the inflation device comprises a barrel and a plunger, the plunger slidably disposed within the barrel and moveable between a plunger first position and a plunger second position; and wherein movement of the plunger from the plunger first position to the plunger second position moves the balloon from the first deflated configuration to the second inflated configuration.

* * * * *